(12) United States Patent
Kaula et al.

(10) Patent No.: US 9,375,582 B2
(45) Date of Patent: Jun. 28, 2016

(54) TOUCH SCREEN SAFETY CONTROLS FOR CLINICIAN PROGRAMMER

(75) Inventors: Norbert Kaula, Arvada, CO (US); Yohannes Iyassu, Denver, CO (US)

(73) Assignee: Nuvectra Corporation, Plano, TX (US)

( * ) Notice: Subject to any disclaimer, the term of this patent is extended or adjusted under 35 U.S.C. 154(b) by 230 days.

(21) Appl. No.: 13/601,504

(22) Filed: Aug. 31, 2012

(65) Prior Publication Data
US 2014/0067013 A1 Mar. 6, 2014

(51) Int. Cl.
*A61N 1/372* (2006.01)
*A61N 1/36* (2006.01)

(52) U.S. Cl.
CPC ........ *A61N 1/37247* (2013.01); *A61N 1/36142* (2013.01); *A61N 1/36132* (2013.01); *A61N 1/37211* (2013.01); *A61N 1/37252* (2013.01)

(58) Field of Classification Search
CPC ........... A61N 1/36142; A61N 1/37247; A61N 1/36132; A61N 1/37211; A61N 1/37252
USPC ...................... 600/300; 607/2, 32, 59, 60, 63
See application file for complete search history.

(56) References Cited

U.S. PATENT DOCUMENTS

| | | | |
|---|---|---|---|
| 4,432,360 A | 2/1984 | Mumford et al. | |
| 5,286,202 A | 2/1994 | De Gyarfas et al. | |
| 5,304,206 A | 4/1994 | Baker, Jr. et al. | |
| 5,312,446 A | 5/1994 | Holschbach et al. | |
| 5,370,672 A | 12/1994 | Fowler et al. | |
| 5,383,914 A | 1/1995 | O'Phelan | |
| 5,421,830 A | 6/1995 | Epstein et al. | |
| 5,628,776 A | 5/1997 | Paul et al. | |
| 5,713,937 A | 2/1998 | Nappholz et al. | |

(Continued)

FOREIGN PATENT DOCUMENTS

| EP | 1192972 | 4/2002 |
|---|---|---|
| EP | 2277586 | 1/2011 |

(Continued)

OTHER PUBLICATIONS

Synalink Features, SynaMed Web Page, http://synamed.com/synalinkFeatures.html., Copyright 2010, 2 pp.

(Continued)

*Primary Examiner* — Christopher D Koharski
*Assistant Examiner* — Pamela M Bays
(74) *Attorney, Agent, or Firm* — Haynes and Boone, LLP; Eric Q. Li

(57) ABSTRACT

The present disclosure involves an electronic apparatus for programming an implantable medical device to provide a stimulation therapy for a patient. The electronic apparatus includes a user interface configured to communicate with a user, a memory storage configured to store executable instructions, and a computer processor configured to execute the instructions to implement a plurality of safety controls. The safety controls include: starting/stopping the stimulation therapy by starting the stimulation therapy after a predefined time delay but stopping the stimulation therapy instantaneously; disabling programming of the electronic apparatus and terminating any existing stimulation therapy in response to a low-battery status of the electronic apparatus; adjusting a value of a stimulation parameter of the stimulation therapy one predetermined step at a time, each adjustment corresponding to a separate user input; and restricting a range in which the user can set an upper limit and a lower limit of the stimulation parameter.

32 Claims, 13 Drawing Sheets

(56) References Cited

U.S. PATENT DOCUMENTS

| | | |
|---|---|---|
| 5,722,999 A | 3/1998 | Snell |
| 5,724,996 A | 3/1998 | Piunti |
| 5,819,740 A | 10/1998 | Muhlenberg |
| 5,879,374 A | 3/1999 | Powers et al. |
| 5,905,500 A | 5/1999 | Kamen et al. |
| 5,938,690 A | 8/1999 | Law et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,345,200 B1 | 2/2002 | Mouchawar et al. |
| 6,386,882 B1 | 5/2002 | Linberg |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Weidenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnet |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B1 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | KenKnight et al. |
| 7,822,483 B2 | 10/2010 | Stone et al. |
| 7,853,323 B2 | 12/2010 | Goetz |
| 7,885,712 B2 | 2/2011 | Goetz et al. |
| 7,890,180 B2 | 2/2011 | Quiles et al. |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | LaLonde et al. |
| 7,991,482 B2 | 8/2011 | Bradley |
| 8,014,863 B2 | 9/2011 | Zhang et al. |
| 8,021,298 B2 | 9/2011 | Barid et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2003/0055406 A1* | 3/2003 | Lebel et al. ............. 604/891.1 |
| 2003/0074037 A1* | 4/2003 | Moore et al. ............... 607/63 |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2004/0049233 A1* | 3/2004 | Edwards ............ A61N 1/3931 607/5 |
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0240244 A1* | 10/2005 | Leinders ............ A61N 1/36071 607/46 |
| 2005/0277872 A1 | 12/2005 | Colby et al. |
| 2006/0089684 A1* | 4/2006 | Blaha ................ A61N 1/37223 607/60 |
| 2006/0089888 A1 | 4/2006 | Roger |
| 2006/0100832 A1 | 5/2006 | Bowman |
| 2006/0217775 A1* | 9/2006 | Mills ................ A61N 1/3925 607/27 |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |

(56) References Cited

U.S. PATENT DOCUMENTS

| | | |
|---|---|---|
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgenson |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281595 A1* | 11/2009 | King et al. ............... 607/46 |
| 2009/0281596 A1 | 11/2009 | King et al. |
| 2010/0004033 A1 | 1/2010 | Choe et al. |
| 2010/0010392 A1* | 1/2010 | Skelton et al. ............ 600/595 |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennett et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Connor et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 0209808 | 2/2002 |
| WO | WO 0284637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pp.

* cited by examiner

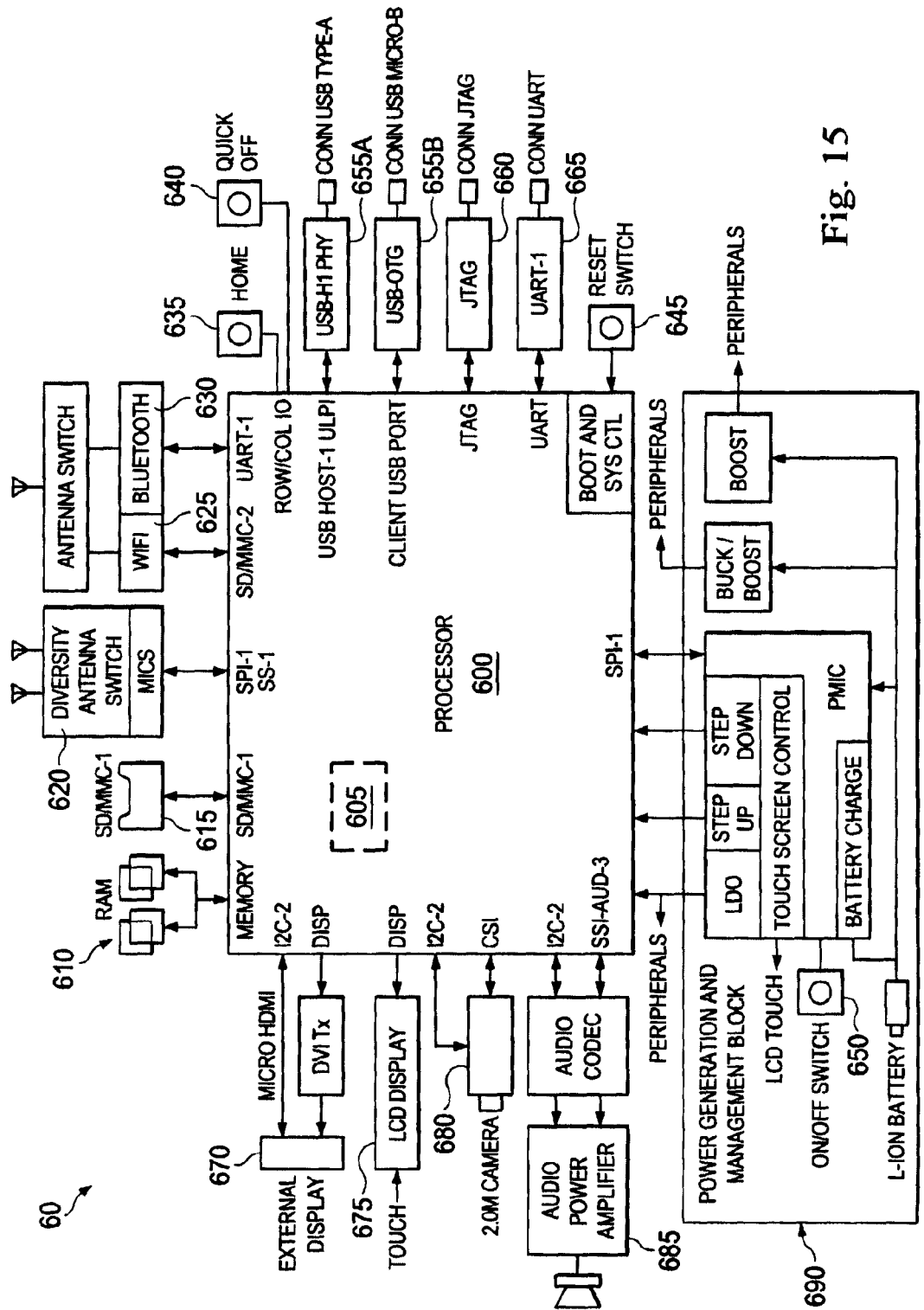

TOUCH SCREEN SAFETY CONTROLS FOR CLINICIAN PROGRAMMER

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients.

An implanted medical device (for example a neurostimulator) can be controlled using an electronic programming device such as a clinician programmer or a patient programmer. These programmers can be used by medical personnel or the patient to define the particular electrical stimulation therapy to be delivered to a target area of the patient's body or alter one or more parameters of the electrical stimulation therapy. Advances in the medical device field have improved these electronic programmers. However, existing electronic programmers may still have shortcomings such as insufficient safety control mechanisms.

Therefore, although electronic programming devices for controlling implanted medical devices have been generally adequate for their intended purposes, they have not been entirely satisfactory in every aspect.

SUMMARY

One of the broader forms of the present disclosure involves electronic device configured to program a medical device implantable in a patient. The electronic device includes: a touch screen display configured to communicate with a user; a memory storage component configured to store programming code; and a computer processor configured to execute the programming code to perform the following tasks: detecting a user input through the touch screen display, wherein the detecting is performed at least in part by measuring an amount of time the touch screen display is engaged as a part of the user input; determining whether the medical device is running a treatment for the patient when the user input is detected; instructing the medical device to stop the treatment if the treatment is running, wherein the stopping of the treatment is performed immediately after the user input is detected; instructing the medical device to start the treatment if no treatment is running and if the amount of time the touch screen display is engaged as a part of the user input exceeds a predetermined limit; instructing the medical device to perform no treatment if the amount of time the touch screen display is engaged as a part of the user input does not exceed the predetermined limit; determining whether the electronic device has a low-battery status; and implementing one of the following measures in response to the low-battery status of the electronic device: disabling programming of the electronic device; stopping an ongoing treatment; and preventing a prospective treatment.

Another one of the broader forms of the present disclosure involves a medical system. The medical system includes: an implantable medical device configurable to deliver a medical therapy to a patient, the medical therapy including a plurality of configurable therapy parameters; and an electronic programmer communicatively coupled to the medical device, wherein the electronic programmer is programmable to configure the therapy parameters of the medical therapy, and wherein the electronic programmer includes a touch-sensitive user interface configured to perform the following actions: displaying one or more virtual objects that represent initiating and terminating a delivery of the medical therapy to the patient; sensing, from a user, an actuation of the one or more virtual objects; terminating the delivery of the medical therapy immediately if the actuation of the one or more virtual objects corresponds to terminating the delivery of the medical therapy; initiating the delivery of the medical therapy in a delayed manner if the actuation of the one or more virtual objects corresponds to starting the delivery of the medical therapy; monitoring a battery level of the electronic programmer; and performing at least one of the following tasks if the battery level is lower than a target battery level: disallowing programming of the electronic programmer; terminating the delivery of an existing medical therapy; and precluding the delivery of a prospective medical therapy.

Yet another one of the broader forms of the present disclosure involves a method of providing safety controls for an electronic programmer configured to program an implantable medical device. The method includes: receiving a request, from a user via a touch screen interface of the electronic programmer, to start or stop an electrical stimulation program; determining whether the user intends to start the electrical stimulation program or to stop the electrical stimulation program; if it has been determined that the user intends to start the electrical stimulation program, starting the electrical stimulation program if the request indicates that the touch screen interface has been engaged by the user for a period of time exceeding a predefined threshold; if it has been determined that the user intends to stop the electrical stimulation program, stopping the electrical stimulation program immediately; querying a battery level of the electronic programmer; and performing at least one of the following actions if the battery level obtained by the querying is less than a predefined battery level: disabling programming of the electronic programmer, stopping an electrical stimulation program in progress, and preventing activation of a prospective electrical stimulation program.

One more of the broader forms of the present disclosure involves an electronic apparatus for programming an implantable medical device to provide a stimulation therapy for a patient. The electronic apparatus includes: user interface means for communicating with a user; memory storage means for storing executable instructions; and computer processor means executing the instructions for implementing a plurality of safety controls including: starting and stopping the stimulation therapy by starting the stimulation therapy after a predefined time delay but stopping the stimulation therapy instantaneously; disabling programming of the electronic apparatus and terminating any existing stimulation therapy in response to a low-battery status of the electronic apparatus; adjusting a value of a stimulation parameter of the stimulation therapy one predetermined step at a time, each adjustment corresponding to a separate user input; and restricting a range in which the user can set an upper limit and a lower limit of the stimulation parameter.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 15 is a simplified block diagram of an electronic programmer according to various aspects of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Electronic programmers have been used to configure or program active implanted medical devices such as neurostimulators so that they can be operated in a certain manner. These electronic programmers include clinician programmers and patient programmers, each of which may be a handheld device. A clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. However, existing programmers in the medical field may still have drawbacks. One such drawback is the lack of comprehensive safety controls. For example, the electronic programmers may be inadvertently programmed to exceed safe or comfortable pain/stimulation thresholds for a patient undergoing treatment. As another example, the power supply or battery life of the electronic programmer may be depleted while applications are still running or while the medical professional is in the middle of providing input, which may lead to unpredictable or undesirable situations. As a further example, if the electronic programmer utilizes a touch screen to receive programming input—for example if gesture-sensitive dials or sliders are used—the interpreted input corresponding to the user's gestures (for example, flickering gestures) may very well exceed the user's intended input. In each of these scenarios, the end result may be patient pain or discomfort. Consequently, the patient may view the electronic programmers or the implanted medical device as unreliable and unsafe, while medical devices should always be, and be seen as, reliable and safe.

To overcome these problems associated with existing electronic programmers, a system of safety controls is implemented on an electronic programmer according to various aspects of the present disclosure.

Figure 1:
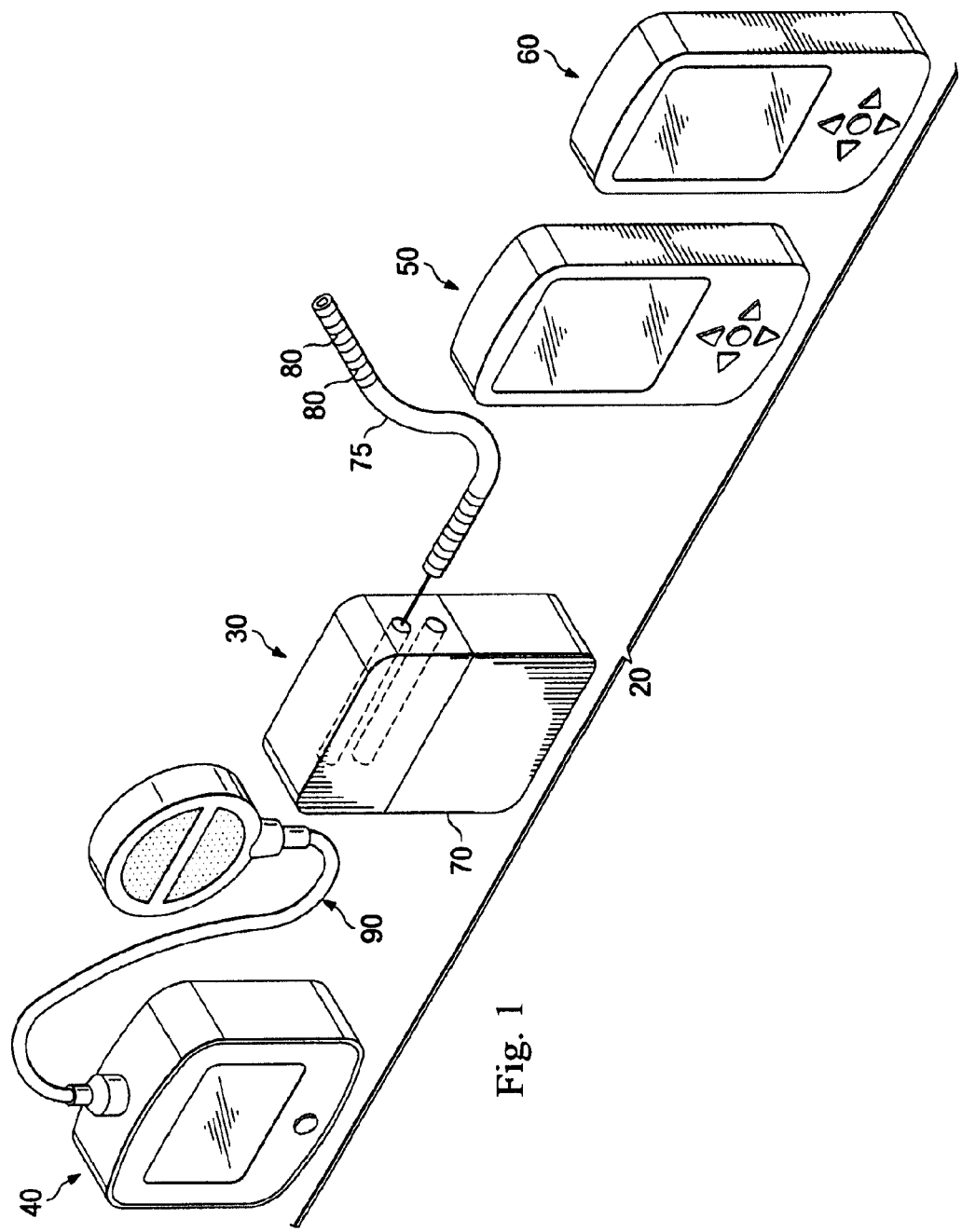
FIG. 1 is a simplified block diagram of an implanted medical system according to various aspects of the present disclosure.

Referring to FIG. 1, a simplified block diagram of an implanted medical device system 20 is illustrated to provide an example context of the various aspects of the present disclosure. The implanted medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end of one or more percutaneous, or skin-penetrating, leads. The other end of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer for which safety controls can be implemented. However, it is understood that the safety controls according to the present disclosure may also be implemented in the patient programmer 50 or other touch screen programming devices (such as smart-phones or tablet computers) in other embodiments. Regardless of the programming device used, the safety controls of the present disclosure are implemented through a touch screen or touch-sensitive user interface installed on the programming device.

Figure 2:
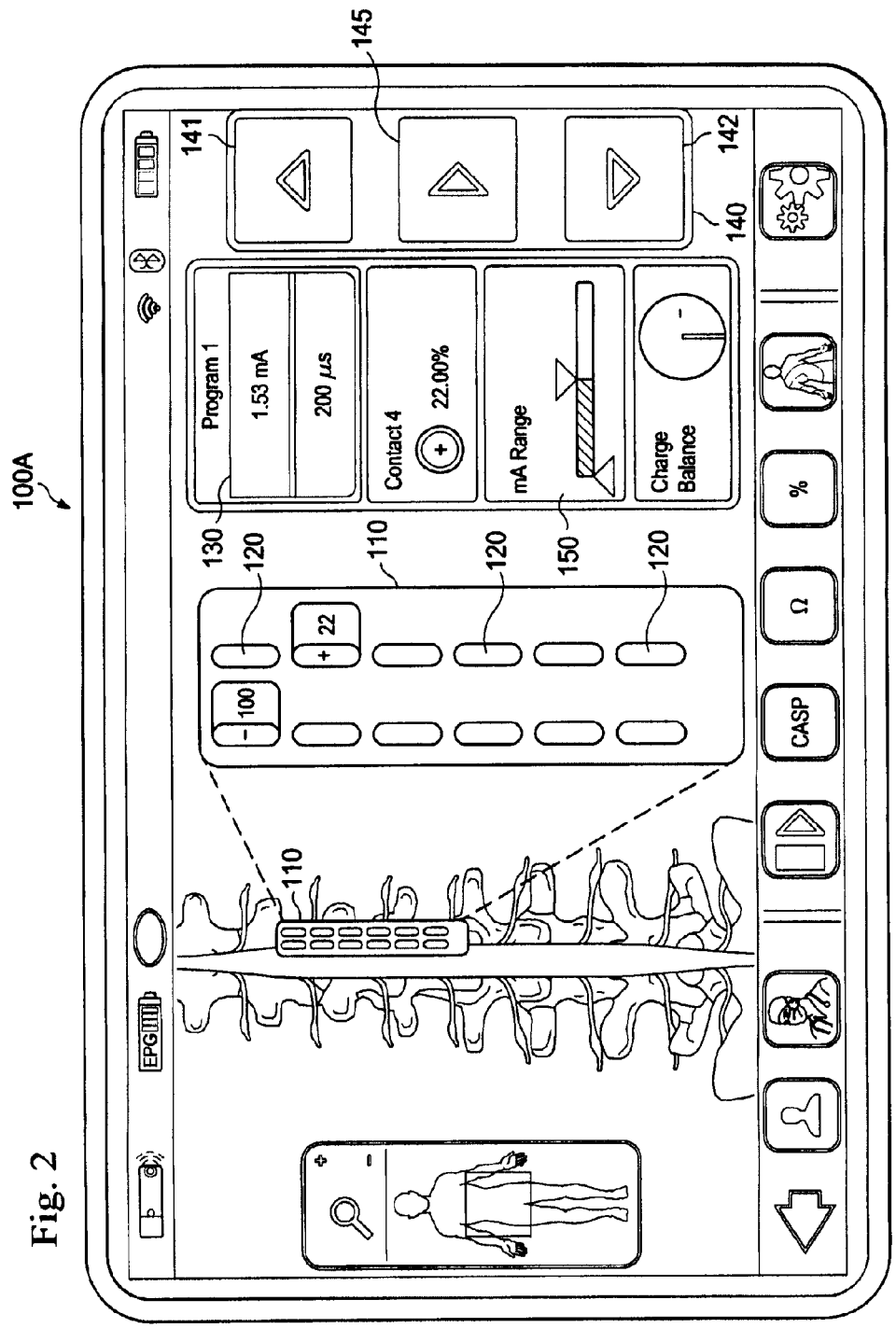
FIGS. 2-7 are various example user interfaces for performing safety controls according to various aspects of the present disclosure.

FIGS. 2-7 are examples of user interfaces 100 that illustrate various aspects of safety controls according to the present disclosure. In more detail, referring to FIG. 2, the user interface 100A illustrate how a user (e.g., a medical professional) can program stimulation parameters for an implanted lead 110. The lead 110 may be a paddle lead, as is shown in the example of FIG. 2, or other types of suitable leads. The lead 110 may contain a plurality of electrode contacts 120 through which electrical current may be delivered to the patient's target tissue areas, thereby helping the patient achieve paresthesia and relieve pain. Each electrode contact 120 may be configured to be a cathode (indicated by the "−" sign) or an anode (indicated by the "+" sign), so that the electrode contact can either sink or source current. The amount of current sunk or sourced by the electrode contact being programmed is shown in a programming box 130. As an example, a selected electrode contact ("Contact 4") of FIG. 2 is being programmed to have an electrical current of 1.53 milliamps (mA).

A programming box 140 is used to set the value of the stimulation electrical current. In the embodiment shown in FIG. 2, the programming box 140 contains buttons 141-142 that are used to increment and decrement the value of the stimulation current shown in the programming box 130. Each press of the button 141 or 142 increments or decrements the value of the stimulation current by a predefined unit, for example 0.01 mA.

In alternative embodiments, other suitable visual mechanisms may be used to increment and decrement the value of the stimulation current. For example, a spring-loaded toggle switch (not illustrated herein) that can be flipped up or down from a resting center position may be used. The toggle switch normally rests in a center position. When the toggle switch is flipped up, it corresponds to incrementing the stimulation current. When the toggle switch is flipped down, it corresponds to decrementing the stimulation current. In more alternative embodiments, the visual mechanism may include a slider.

The programming box 140 also contains a run/stop button 145. The run/stop button 145 is used to run a stimulation program or to stop a stimulation program. In other embodiments, the run/stop button 145 may be implemented as two separate buttons, one serving as the "run" button, while the other serving as the "stop" button.

Still referring to FIG. 2, the user interface 100A also shows a programming box 150, which allows the user to set an upper limit and a lower limit for the amount of the programmed electrical stimulation current. These upper and lower stimulation current limits may be programmed by a sliding bar, as shown in FIG. 2, or by other suitable mechanisms (for example text fields) in other embodiments. As the user drags his finger across the sliding bar, different upper and lower limits may be set for the programmed stimulation current.

According to one aspect of the safety controls of the present disclosure, the upper limit of the stimulation current cannot be changed to a value less than the presently programmed value, and the lower limit of the stimulation current cannot be changed to a value greater than the presently programmed value. In other words, the upper limit cannot be programmed to be less than 1.53 mA, and the lower limit cannot be programmed to be greater than 1.53 mA in the example illustrated in FIG. 2. These restrictions on the programmed current limits are imposed to prevent logical inconsistencies, since the presently programmed stimulation current value should lie between the upper and lower limits. The reason for the lower limit is for the physician to mark the current level that the patient begins to perceive stimulation. Anything below that is not felt therefore is not a desired stimulation amplitude. The reason for the upper limit is that anything above that is painful for the patient.

According to another aspect of the safety controls of the present disclosure, the incrementing/decrementing of the value of the stimulation current is done one step at a time. As discussed above, the step may be a predefined unit such as 0.01 mA. Thus, each press of the button 141 or 142 (or a flip of the toggle switch, in embodiments where the toggle switch is used) results in the value of the stimulation current being incremented or decremented only by one unit, even if the button 141 or 142 is held down continuously. Stated differently, holding down the button 141 or 142 will not result in the value of the programmed stimulation current to be incremented or decremented continuously. This aspect of the safety controls helps prevent accidental or unintentional overstimulation (i.e., by incrementing the current too fast) or understimulation (i.e., by decrementing the current too fast). Instead, since the stimulation current is incremented one small step at a time, its value changes slowly, which gives the patient and the user of the electronic programmer ample time to make appropriate adjustments.

According to yet another aspect of the safety controls of the present disclosure, the run/stop button 145 employs a delayed start, while stopping is instantaneous. For example, to start a stimulation program, the run/stop button needs to be held down for longer than a predetermined period of time. The predetermined period of time may be a few seconds in some embodiments. In this manner, if a user merely taps or presses the run/stop button 145 briefly, the stimulation program will not be executed. This safety control feature ensures that the execution of the stimulation program is most likely intentional—since the button was held down for a while—rather than accidental or inadvertent. Meanwhile, the stimulation program may be immediately halted by a mere tapping or pressing of the run/stop button 145. Stated differently, the stopping of the stimulation program is instantaneous. This safety control feature ensures that the patient can be relieved from undesirable stimulation as quickly as possible.

Figure 3:
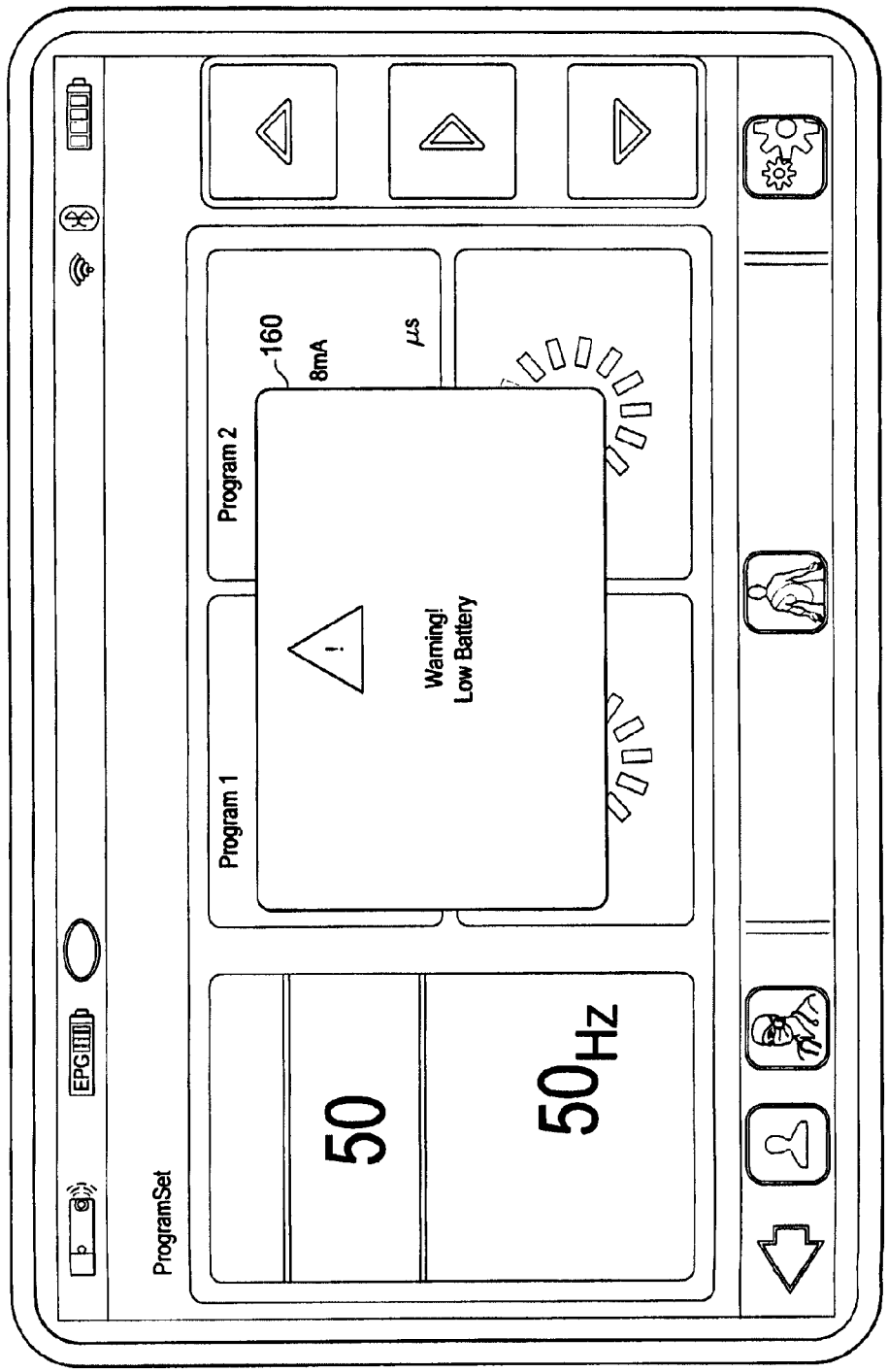

Referring now to FIG. 3, the user interface 100B displays a warning message 160 when a battery of the electronic programmer is running low. In some embodiments, the battery level of the electronic programmer is periodically queried (note that the periodic querying herein need not necessarily be performed at evenly-spaced time intervals). When the querying results indicate that the battery level has dropped below a predefined threshold, for example 5% or 10% of its full capacity, the user interface 100B displays the warning message 160 to alert the user of the electronic programmer of the low battery status. This low-battery warning feature may not be commonly available on conventional electronic programmers for medical devices. Here, it serves a useful purpose as it gives the user an opportunity to remedy the low battery situation (for example by recharging it) before the low battery situation causes problems.

If the low battery situation is not timely resolved, another safety control feature of the present disclosure involves preventing the programming of stimulation parameters while the battery level is extra low. For example, referring to FIG. 4, the user interface 100C displays an error message 170 if the user attempts to program stimulation parameters while the battery level is extra low, which is below another predefined threshold that is even less than the predefined threshold for which a warning is displayed. For instance, a 10% battery level may be considered low battery to trigger a low-battery warning, whereas a 2% battery level may be considered an extra-low battery to trigger the extra-low battery error message 170. The error message 170 may read, as an example, "Error! Programming Prevented Due to Low Battery."

Figure 4:
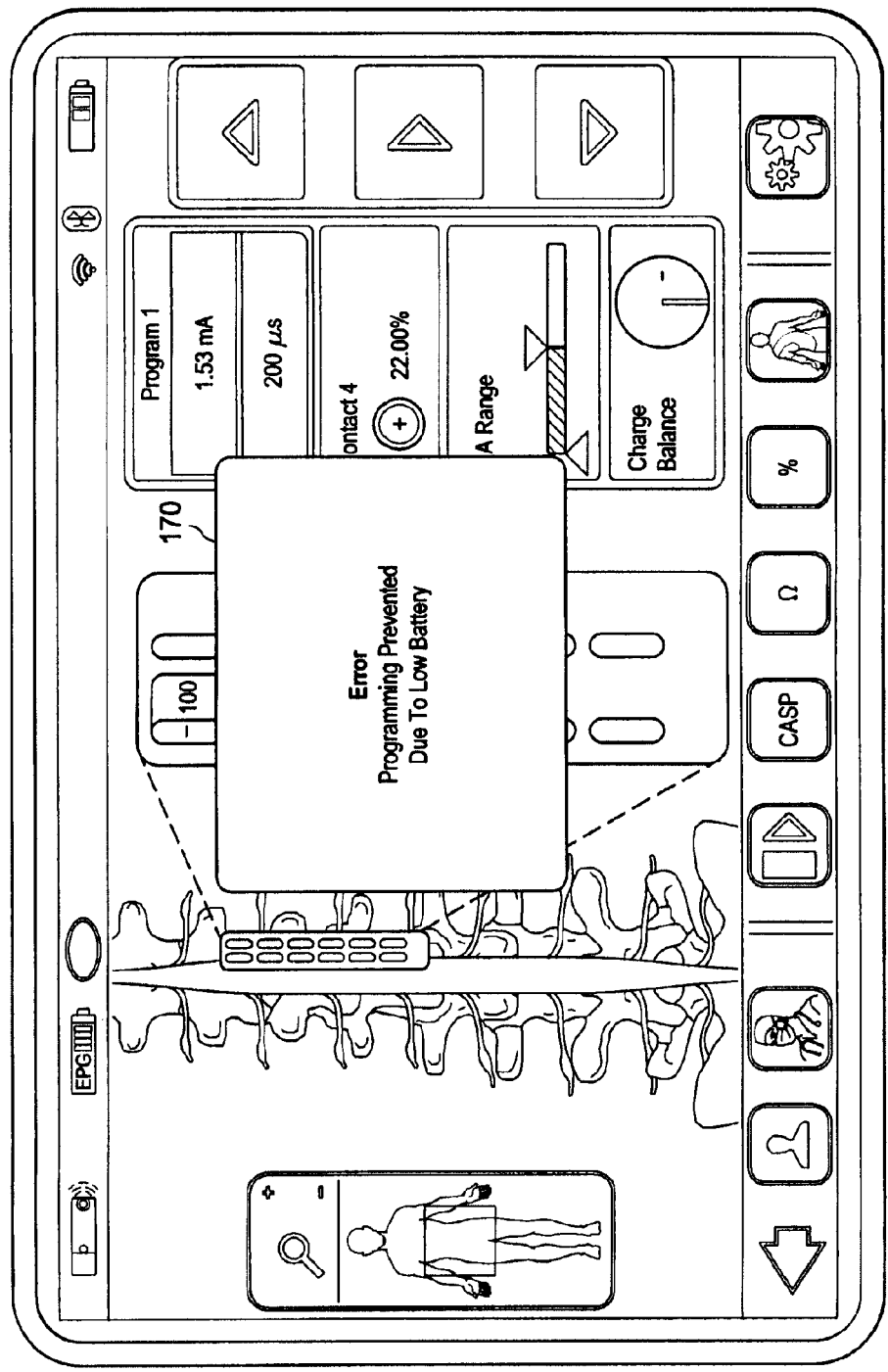
Figure 5:
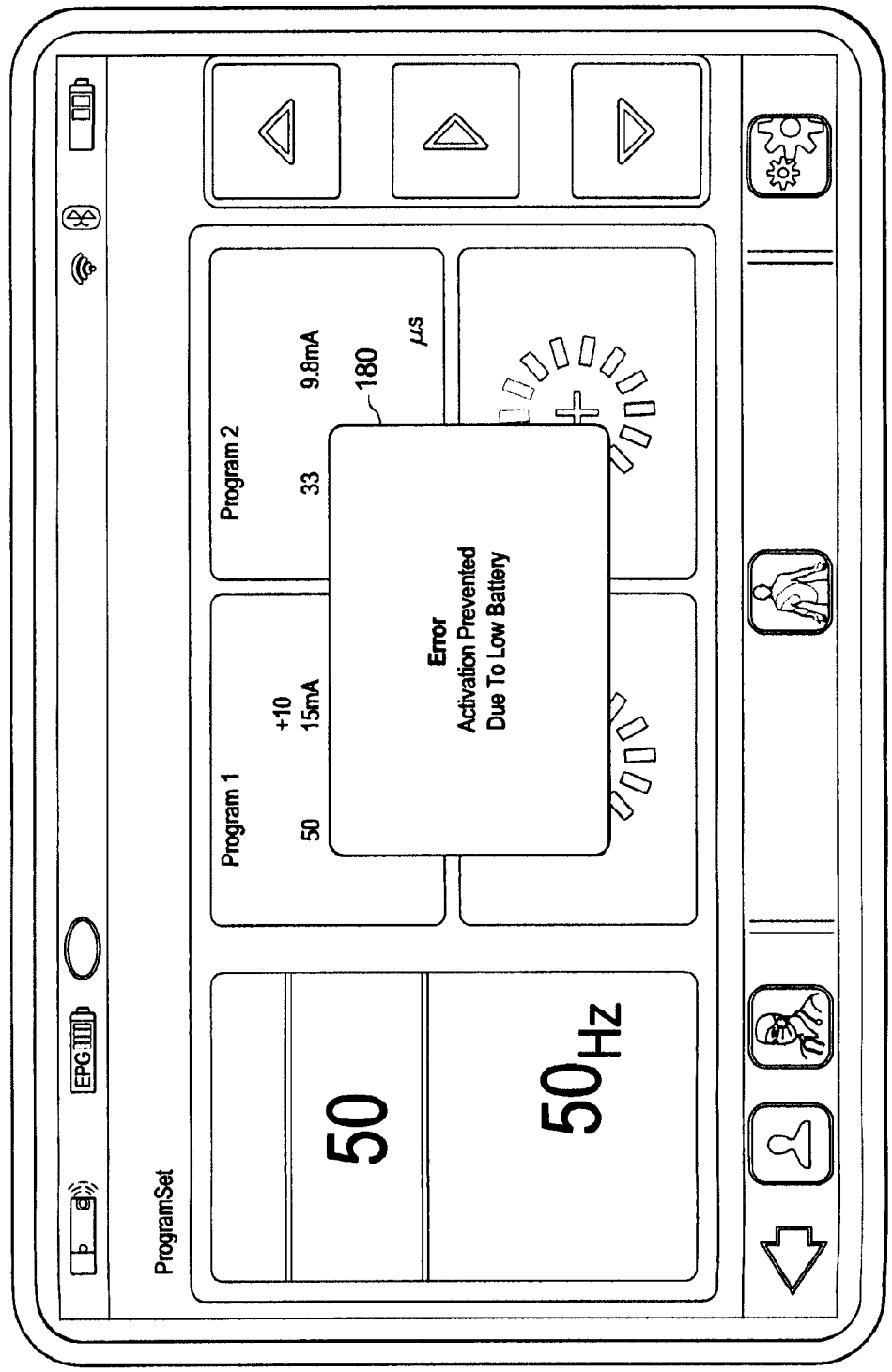
Figure 6:
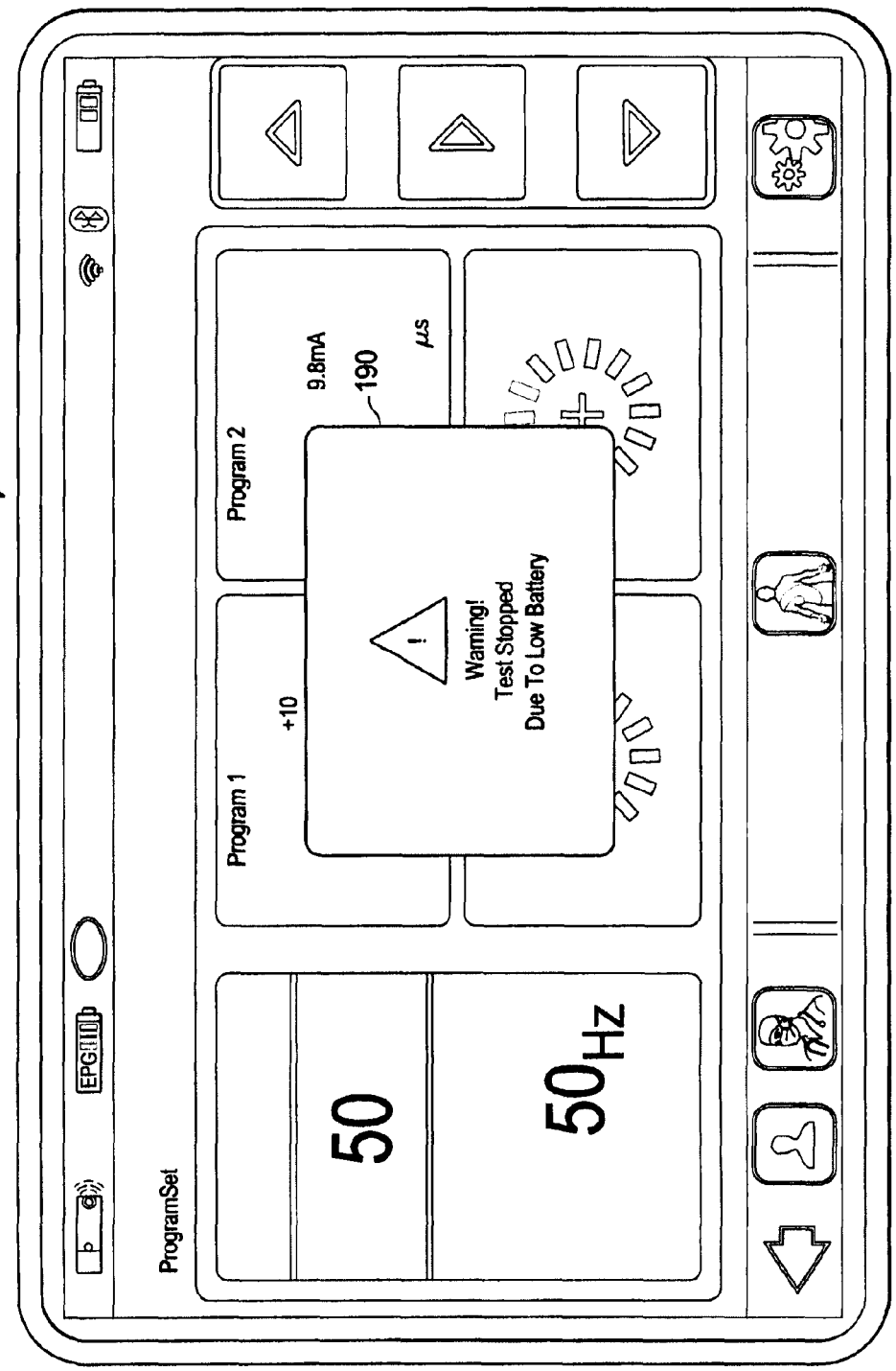
Figure 7:
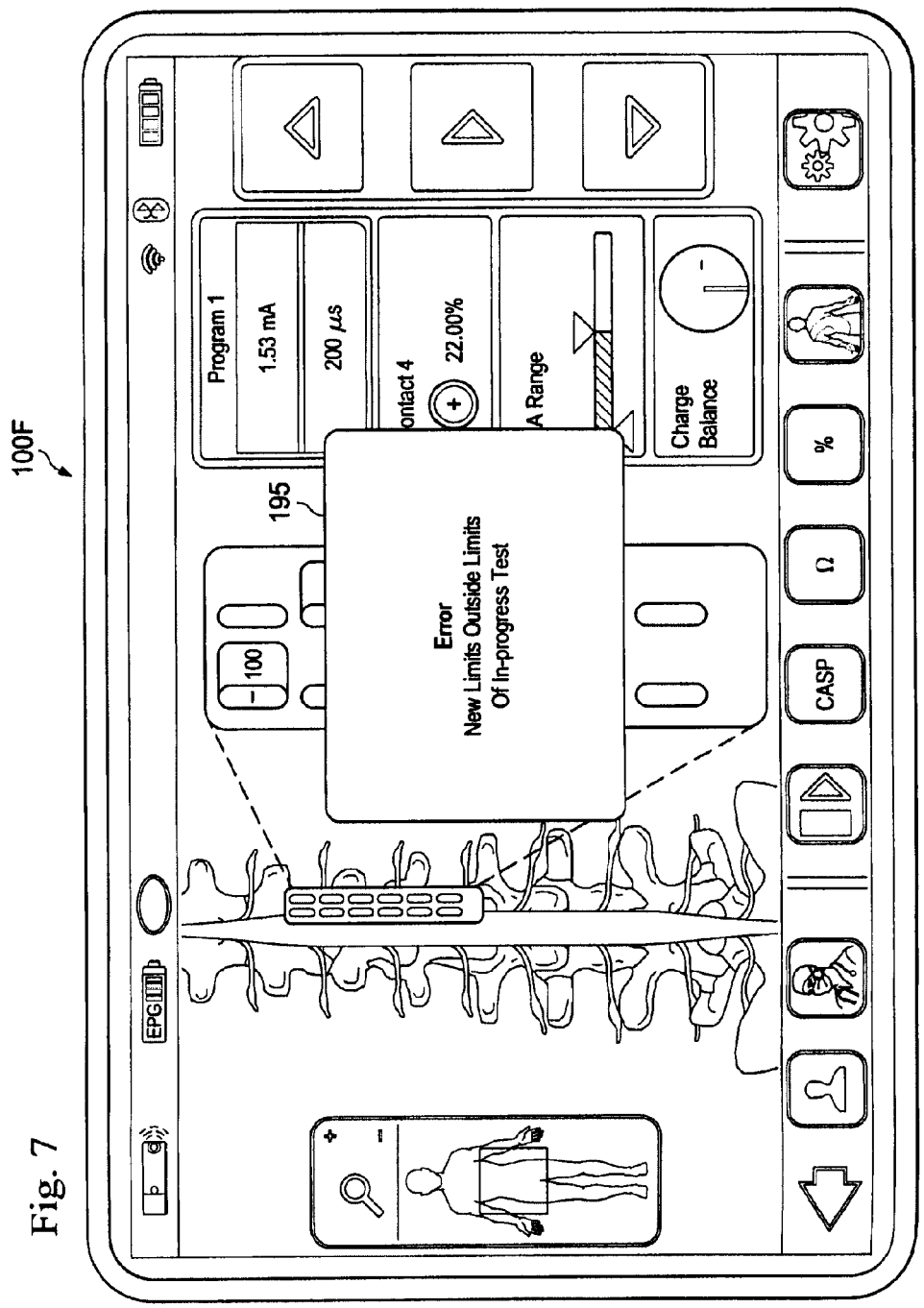

The safety control feature illustrated in FIG. 4 helps prevent erroneous or incomplete programming. In conventional electronic programmers where such feature is not implemented, a sudden unexpected death of the battery may occur. When that happens, it may result in incomplete and/or unpredictable stimulation programming, which may cause unnecessarily prolonged pain or discomfort for the patient. The electronic programmer of the present disclosure avoids such problems by effectively not allowing a user to engage in the dangerous and risky task of programming stimulation parameters while the battery of the programmer is running extra low.

Similarly, another safety control feature of the present disclosure involves preventing the activation of stimulation tests when the battery level is extra low. For example, referring to FIG. 5, the user interface 100D displays an error message 180 if the user attempts to activate a stimulation test while the battery level is extra low. The error message 180 may read, as an example, "Error! Activation Prevented Due to Low Battery." This safety control feature helps prevent a scenario (possible with conventional programmers) where the battery of the electronic programmer runs out during a stimulation test. In that scenario, the stimulation may continue for a short period of time even though the electronic programmer can no longer control the stimulation. If the patient finds the stimulation uncomfortable, he will unfortunately have to suffer through the uncomfortable stimulation until the stimulation ends. In comparison, this safety control feature herein prevents such scenario from occurring in the first place.

Yet another safety control feature of the present disclosure involves automatically stopping the stimulation tests when the battery level is extra low. For example, referring to FIG. 6, if a stimulation test is in progress, and the battery of the electronic programmer reaches an extra low level status, the user interface 100E may display a warning message 190 to the user. The warning message 190 may read, as an example, "Warning! Test Stopped Due to Low Battery." Meanwhile, the stimulation test is automatically shut down in a graceful manner. This safety control feature helps prevent sudden and unexpected stop of stimulation tests. In more detail, without this safety feature, and the programmer abruptly shuts down the stimulation test due to low battery, it may be uncomfortable for the patient. Here, the stimulation tests may be shut down more gradually, for example in a "ramp down" mode. Such shutdown of stimulation provides the patients a more pleasant experience than a sudden and abrupt shutdown, which is outside the control of the clinician programmer.

Another safety control feature of the present disclosure involves preventing a user from making certain changes to stimulation parameter limits during stimulation. For example, referring to FIG. 7, if the user attempts to set parameter limits outside existing limits while a stimulation test is in progress, the new parameter limits will not be set, and the user interface 100F may display an error message 200 that reads, for example, "Error! New Limits Outside Limits of In-Progress Test." For example, if the existing upper limit for stimulation current is 2 mA, and the user attempts to change the upper limit to 4 mA during stimulation, the user interface 100F may display the error message 200 to the user and will not allow the new upper limit to be entered.

These various safety features discussed above and their respective methods of operation are illustrated in FIGS. 8-14, which contain flowcharts. These flowcharts will now be described in more detail below.

Figure 8:
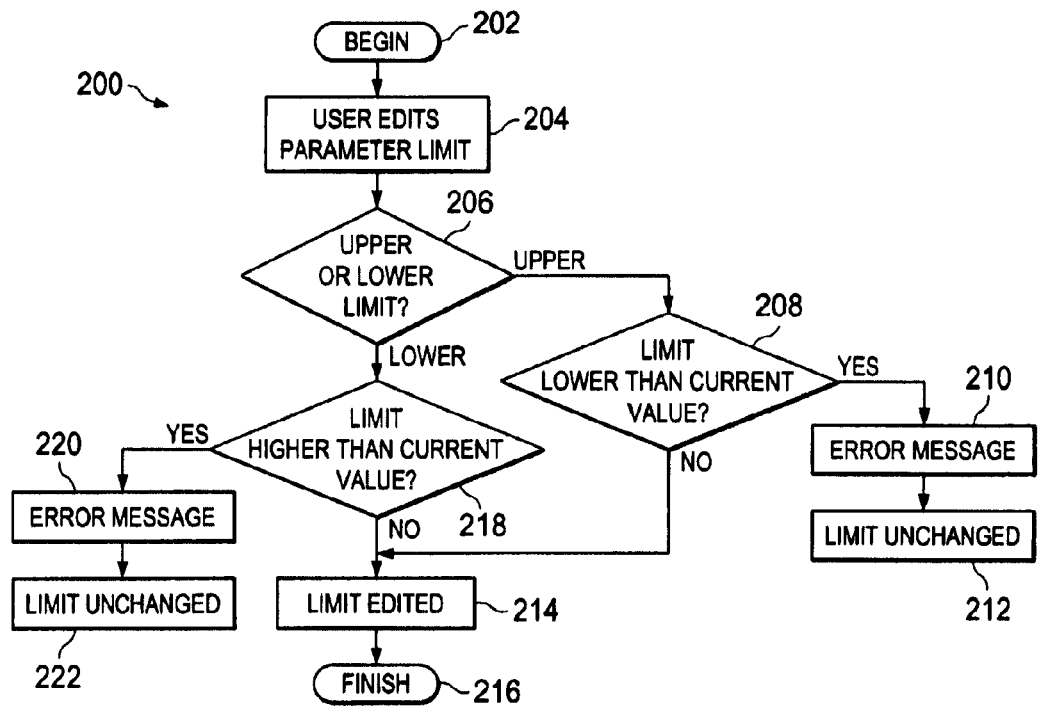
FIGS. 8-14 are flowcharts of various methods for performing safety controls according to various aspects of the present disclosure.

FIG. 8 is a flowchart of a method 200 of implementing stimulation parameter limit safety controls according to the various aspects of the present disclosure. As discussed above with reference to FIG. 2, if a user wishes to set new stimulation parameter limits, the new upper limit should be greater than the existing upper limit, and the new lower limit should be less than the existing lower limit. In more detail, the method 200 begins with a step 202. Thereafter, the user—which may be a medical professional such as a physician or a nurse—edits the parameter limits in step 204. In a decision step 206, a determination is made as to whether the new limit entered is an upper limit or a lower limit. If it is the upper limit that is being edited, the method 200 proceeds to step 208, which is another decision step to determine whether the new limit entered is lower than the existing upper limit. If the answer is yes, then the method 200 proceeds to step 210, in which an error message is displayed to the user. The upper limit remains unchanged in step 212. On the other hand, if the decision step 208 determines that the new upper limit entered is not lower than the existing upper limit, then the method 200 proceeds to step 214, in which the upper limit is edited (i.e., the new upper limit is accepted). The method 200 may then finish at step 216.

Similarly, going back to the decision step 206, if it is the lower limit that is being edited, the method 200 proceeds to step 218, which is another decision step to determine whether the lower limit entered is greater than the existing lower limit. If the answer is yes, then the method 200 proceeds to step 220, in which an error message is displayed to the user. The upper limit remains unchanged in step 222. On the other hand, if the decision step 218 determines that the new lower limit entered is not greater than the existing lower limit, then the method 200 proceeds to step 214 again, in which the lower limit is edited (i.e., the new lower limit is accepted). The method 200 may then finish again at step 216.

Figure 9:
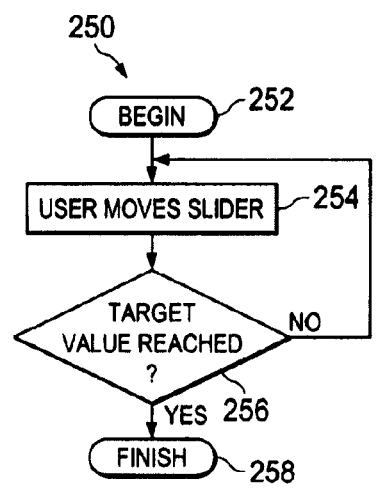

FIG. 9 is a flowchart of a method 250 of incrementing or decrementing the value of a stimulation parameter using a visual mechanism according to the various aspects of the present disclosure. As discussed above with reference to FIG. 2, the visual mechanism may be "up" and "down" buttons, a spring-loaded toggle switch, a slider, or another suitable virtual or physical mechanism. Regardless of the mechanism employed, the incrementing and decrementing of the value of the stimulation parameter occurs one small predefined step at a time. In other words, the user needs to repeatedly perform the appropriate incrementing/decrementing actions (for example pressing the up/down buttons or flipping the toggle switch) until the target value is reached.

An embodiment of this aspect of operation is reflected in the flowchart of the method 250. The method 250 begins with step 252. Thereafter, in step 254, the user's movement of the slider (or any other suitable mechanism) is detected. The method 250 then proceeds to a decision step 256 to determine whether the target value for the stimulation parameter is reached. If the answer is no, then the method proceeds back to step 254, in which the user needs to move the slider again. If the answer is yes, then the method 250 is finished at step 258.

Figure 10:
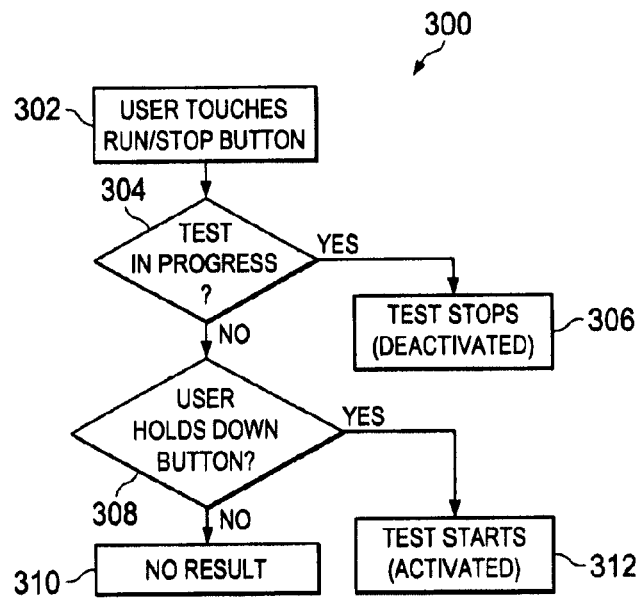

FIG. 10 is a flowchart of a method 300 of running/stopping stimulation according to the various aspects of the present disclosure. As discussed above with reference to FIG. 2, the run/stop button has to be held down for some length of time in order to start stimulation, since the delayed start of the stimulation helps prevent accidental stimulation. On the other hand, a single press or tapping of the run/stop button stops stimulation immediately, since the quick shut-down of the stimulation allows the user to end painful or uncomfortable stimulation to the patient as soon as possible.

An embodiment of this aspect of operation is reflected in the flowchart of the method 300. The method 300 begins with step 302, in which a user's engagement of the run/stop button is detected. The user's engagement of the run/stop button may be a tapping or pressing of the run/stop button, for example. The method 300 continues with a decision step 304 to determine whether a stimulation test is currently in progress. If the answer is yes, then the method 300 proceeds to step 306, in which the stimulation test is immediately stopped (i.e., the stimulation test is deactivated). If the answer is no, then the method 300 proceeds to another decision step 308 to determine whether the run/stop button has been held down for a period of time. The period of time required for the run/stop button to be pressed down may need to exceed a predefined threshold (e.g., a few seconds or longer) in order to run the stimulation test. If the answer from the decision step 308 is no, then the method 300 proceeds to step 310, in which nothing happens (i.e., no stimulation is run). If the answer from the decision step is yes, then the method 300 proceeds to step 312, in which the stimulation test starts to run (i.e., stimulation is activated).

Figure 11:
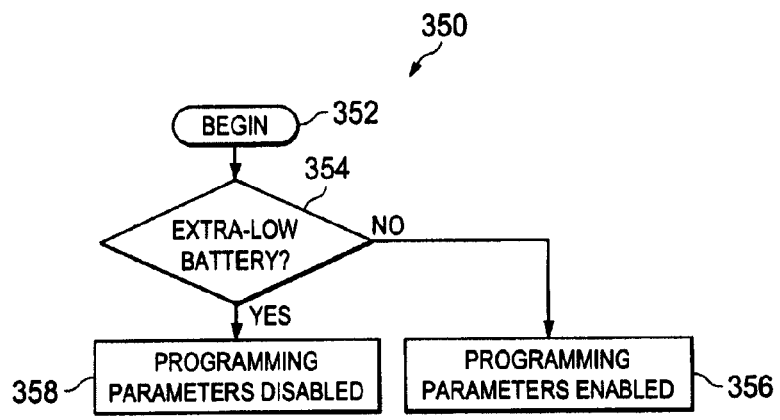

FIG. 11 is a flowchart of a method 350 of disabling stimulation parameter programming in response to an extra low programmer battery level according to the various aspects of the present disclosure. As discussed above with reference to FIG. 4, when the battery level for the electronic programmer is running extra-low, for example below a certain predefined threshold level, an error message is displayed to the user, and stimulation parameter programming will be disabled.

An embodiment of this aspect of operation is reflected in the flowchart of the method 350. The method 350 begins with step 352. Thereafter, the method 350 proceeds to a decision step 354 to determine whether the battery level is running extra low. If the answer from the decision step 354 is no, then the method 350 proceeds to step 356, in which the stimulation parameter programming is enabled. If the answer from the decision step 354 is yes, then the method 350 proceeds to step 358, in which the stimulation parameter programming is disabled.

Figure 12:
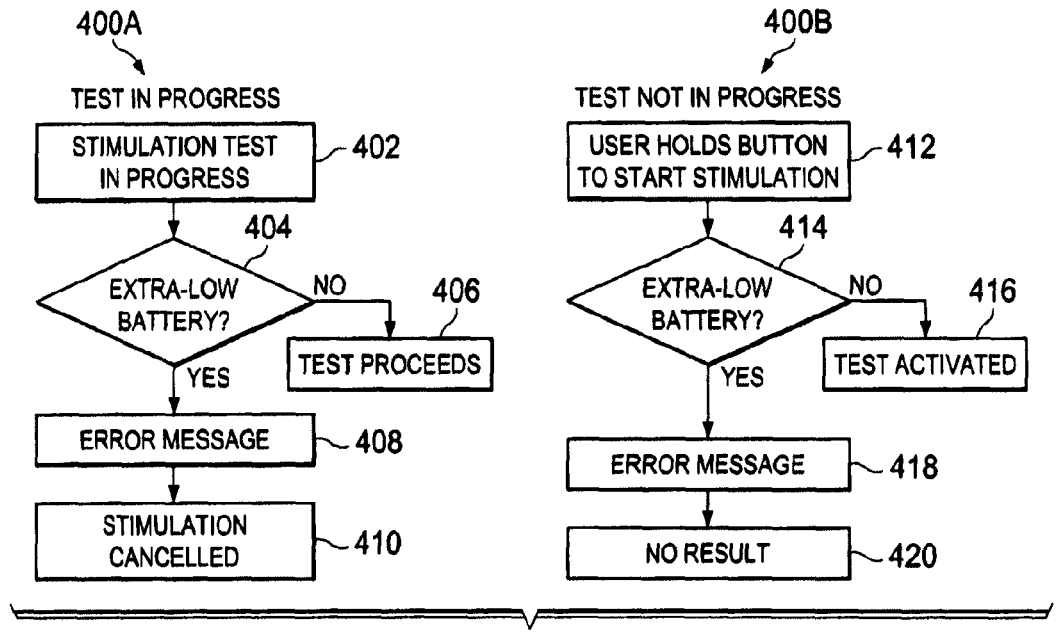

FIG. 12 is a flowchart of a method 400 of preventing stimulation and stopping in-progress tests in response to an extra low programmer battery level according to the various aspects of the present disclosure. As discussed above with reference to FIGS. 5 and 6, when the battery level for the electronic programmer is running extra-low, for example below a certain predefined threshold level, an error message is displayed to the user, and stimulation will be automatically stopped.

An embodiment of this aspect of operation is reflected in the flowchart of the method 400. The method 400 includes sub-methods 400A and 400B, which correspond to a "Test In Progress" scenario and a "Test Not In Progress" scenario, respectively. The sub-method 400A begins with step 402, in which a stimulation test is already in progress. The sub-method 400A continues to a decision step 404 to determine whether an extra-low battery level has been reached. If the answer is no, then the sub-method 400A continues with step 406 to proceed with the stimulation test. If the answer is yes, then the sub-method 400A continues with step 408 to display an error message to the user and cancels the stimulation in step 410.

The sub-method 400B begins with step 412, in which a user's attempt to start stimulation is detected, for example by detecting that the user has held down the run/stop button. The sub-method 400B continues to a decision step 414 to determine whether an extra-low battery level has been reached. If the answer is no, then the sub-method 400B continues with step 416 to activate the stimulation test. If the answer is yes, then the sub-method 400B continues with step 418 to display an error message to the user. Correspondingly, no stimulation will occur, as is indicated by step 420.

Figure 13:
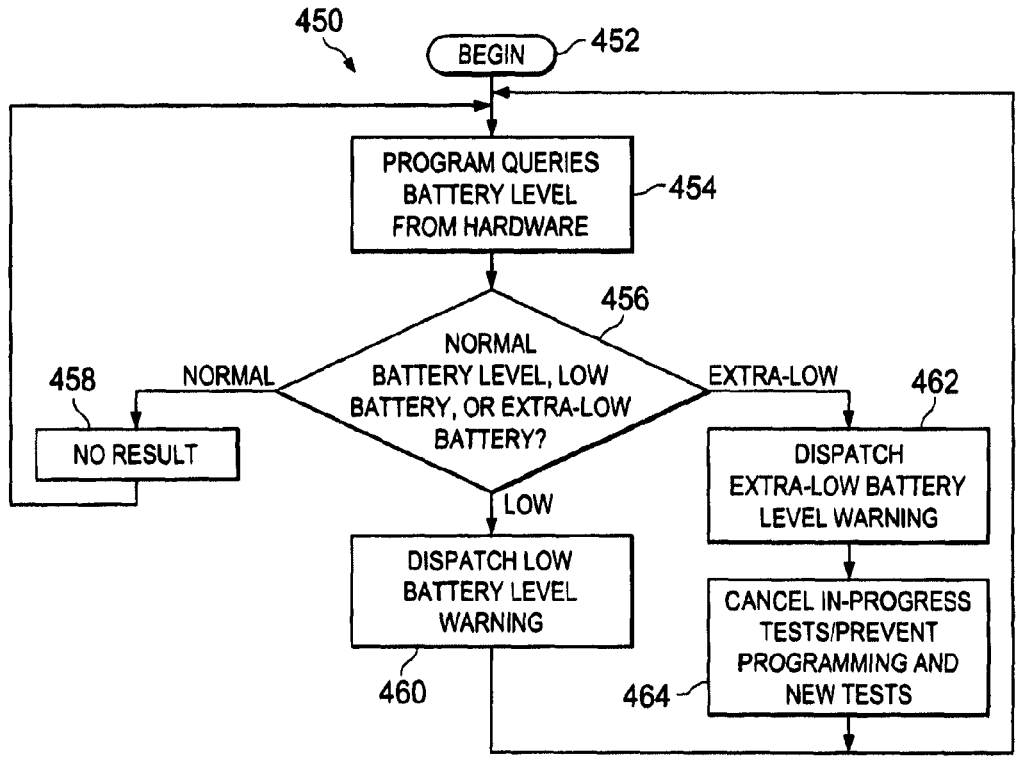

FIG. 13 is a flowchart of a method 450 for performing battery level safety management according to various aspects of the present disclosure. Certain aspects of the methods 350 and 400 discussed above are also integrated and reflected in the method 450. The method 450 begins with step 452. In step 454, the battery level of the electronic programmer is queried. In response to the queried battery level, the method 450 proceeds to a decision step 456 to determine whether the battery level is normal, low, or extra low. If the answer from the decision step 456 is that the battery level is normal, then the method 450 proceeds to step 458, in which no action will be taken, and the method 450 loops back to step 454 to query the battery level again. If the answer from the decision step 456 is that the battery level is low, then the method 450 proceeds to step 460, in which a low battery level warning is dispatched. Thereafter, the method 450 loops back to step 454 to query the battery level again. If the answer from the decision step 456 is that the battery level is extra-low, then the method 450 proceeds to step 462, in which an extra-low battery level warning is dispatched. The method 450 then proceeds to step 464 to cancel in-progress tests and prevents stimulation programming and new tests. Thereafter, the method 450 loops back to step 454 to query the battery level again.

Figure 14:
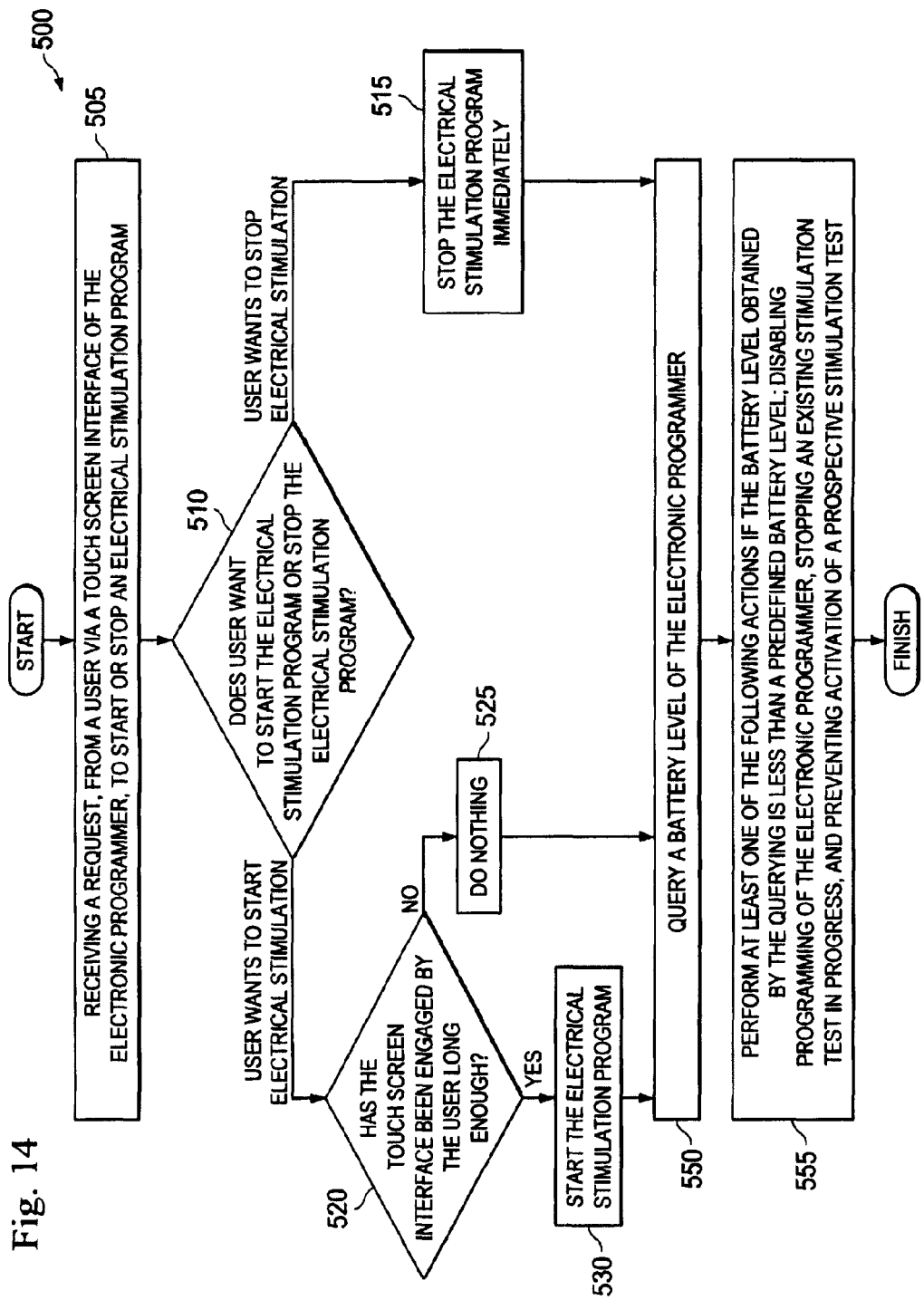

FIG. 14 is a flowchart of a method 500 for providing safety controls for an electronic programmer configured to program an implantable medical device according to various aspects of the present disclosure. The electronic programmer may be a portable handheld clinician programmer in some embodiments. The method 500 includes a step 505, in which a user request to start or stop an electrical stimulation program is received via a touch screen interface of the electronic programmer. In some embodiments, the user is a medical professional. The method 500 proceeds to a decision step 510 to determine whether the user wants to start the electrical stimulation program or to stop the electrical stimulation program. If the step 510 determines that the user wants to stop an already-active electrical stimulation program, then the method 500 proceeds to step 515, in which the electrical stimulation program is stopped immediately.

On the other hand, if the step 510 determines that the user wants to start an electrical stimulation program when no such program is in progress yet, then the method 500 proceeds to a decision step 520 to determine whether the touch screen interface has been engaged by the user for a sufficient time period. If the answer from the decision step 520 is no, then nothing will be done, as reflected in step 525. But if the answer from the decision step 520 is yes, then the electrical stimulation program will be started in step 530.

The method 500 also includes a step 550, in which a battery level of the electronic programmer is queried periodically (though not necessarily at evenly-spaced time intervals). Thereafter, the method 500 proceeds to step 555 to perform at least one of the following actions if the battery level obtained by the querying is less than a predefined battery level: disabling programming of the electronic programmer, stopping an existing stimulation test in progress, and preventing activation of a prospective stimulation test. In some embodiments, the step 55 may also include shutting down the various electronic components of the electronic programmer one or more components at a time in response to a detected low battery level. In other words, when the battery gets low, the electronic programmer begins shutting itself down, starting with less critical components and moving towards the more critical components in a gradual manner. As the battery level becomes lower and lower, more and more electronic components may be shut down.

It is understood that the method 500 may include additional steps that are performed before, during, or after the steps 505-555 discussed above. For example, in some embodiments, the method 500 may include an additional step in which a value of a stimulation parameter is incremented or decremented one predefined step at a time. Each decrement or increment of the stimulation parameter requires a separate user action, for example a click or press of a button via the touch screen interface. As another example, the method 500 may include an additional method step that prevents the user from setting an upper limit of a stimulation parameter to a value less than an existing value of the stimulation parameter. Such method step may also prevent the user from setting a lower limit of a stimulation parameter to a value greater than the existing value of the stimulation parameter.

FIG. 15 shows a block diagram of one embodiment of the clinician programmer (CP) 60 (FIG. 18) that can be used to perform the safety control methods discussed above. It is understood, however, that alternative embodiments of the CP may be used to perform these safety control methods too.

The CP includes a printed circuit board ("PCB") that is populated with a plurality of electrical and electronic components that provide power, operational control, and protection to the CP. With reference to FIG. 15, the CP includes a processor 600. The processor 600 controls the CP. In one construction, the processor 600 is an applications processor model i.MX515 available from Freescale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Freescale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 15 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 15.

The CP includes multiple bi-directional radio communication capabilities. Specific wireless portions included with the CP are a Medical Implant Communication Service (MICS) bi-directional radio communication portion 620, a WiFi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The WiFi portion 625 and Bluetooth portion 630 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 15.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 15) may also be included for data transfer.

It is understood that a patient programmer may be implemented in a similar manner as the clinician programmer shown in FIG. 15. Also, according to the present disclosure, the various safety controls methods discussed above with reference to FIGS. 8-14 may be implemented in an electronic device such as the clinician programmer 60 or a suitable patient programmer. For example, the safety controls may be implemented on the clinician or patient programmers through an appropriate user interface, such as those shown in FIGS. 2-7 discussed above.

Furthermore, though the various safety controls concepts of the present disclosure are explained using an implanted pulse generator (IPG) as an example, it is understood that these safety controls concepts may apply to other types of implanted medical devices as well, such as pacemakers, etc.

Figure 16B:
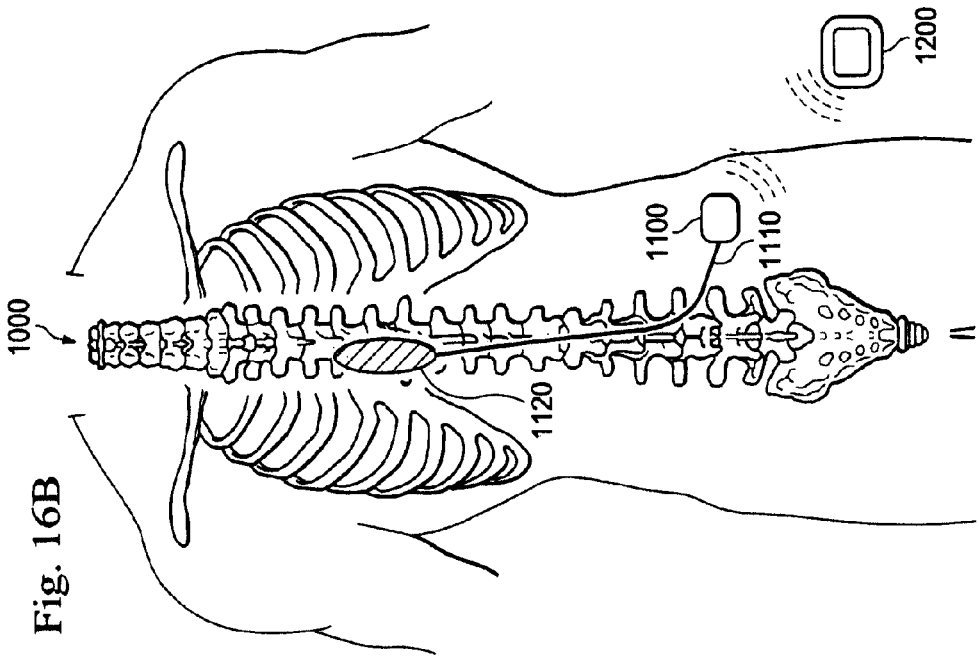
FIGS. 16A and 16B are side and posterior views of a human spine, respectively.
Figure 16A:
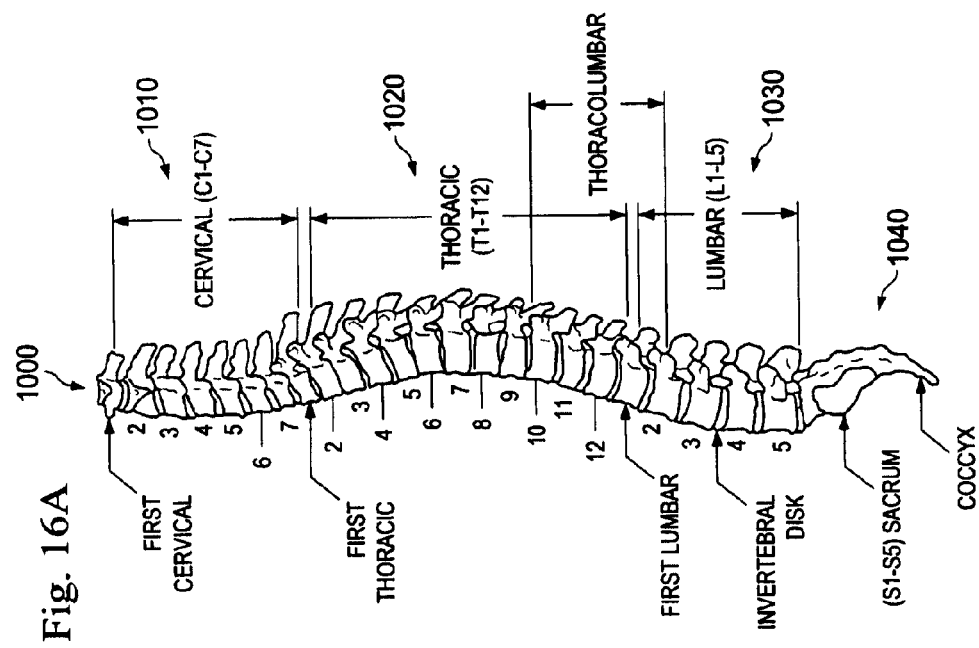

FIG. 16A is a side view of a spine 1000, and FIG. 16B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 16B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 15.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An electronic device configured to program a medical device implantable in a patient, the electronic device comprising:
a touch screen display configured to communicate with a user;
a memory storage component configured to store programming code; and
a computer processor configured to execute the programming code to perform the following tasks:
detecting a user input through the touch screen display, wherein the detecting is performed at least in part by measuring an amount of time the touch screen display is engaged as a part of the user input;
determining whether the medical device is running a treatment for the patient when the user input is detected;
instructing the medical device to stop the treatment if the treatment is running, wherein the stopping of the treatment is performed immediately after the user input is detected;
instructing the medical device to start the treatment if no treatment is running and if the amount of time the touch screen display is engaged as a part of the user input exceeds a predetermined limit;
instructing the medical device to perform no treatment if the amount of time the touch screen display is engaged as a part of the user input does not exceed the predetermined limit;
determining whether the electronic device has a low-battery status; and
implementing one of the following measures in response to the low-battery status of the electronic device:
disabling programming of the electronic device;
stopping an ongoing treatment; and
preventing a prospective treatment.

2. The electronic device of claim 1, wherein the treatment comprises one or more stimulation parameters, and further comprising:
changing a value of the one or more stimulation parameters by one predefined step at a time in response to one or more user actions.

3. The electronic device of claim 2, wherein each change of the value of the one or more stimulation parameters corresponds to a different one of the user actions.

4. The electronic device of claim 1, wherein the treatment comprises one or more stimulation parameters, and further comprising:
restricting a configurable range of an upper limit or a lower limit of one of the stimulation parameters.

5. The electronic device of claim 4, wherein the restricting comprises:
restricting the configurable range of the upper limit of the stimulation parameter to be greater than or equal to a current value of the stimulation parameter; and
restricting the configurable range of the lower limit of the stimulation parameter to be less than or equal to the current value of the stimulation parameter.

6. The electronic device of claim 1, wherein the detecting the user input comprises detecting a click of a virtual button on the touch screen display.

7. The electronic device of claim 1, wherein the determining whether the electronic device has a low-battery status comprises:
continuously monitoring an amount of charge of a battery of the electronic device; and
deeming that the low-battery status has been achieved if the amount of charge of the battery is less than a predetermined amount of charge.

8. The electronic device of claim 1, wherein:
the electronic device includes a portable handheld clinician programmer;
the user includes a healthcare personnel; and
the medical device includes a neurostimulator.

9. An electronic apparatus for programming an implantable medical device to provide a stimulation therapy for a patient, the electronic apparatus comprising:
user interface means for communicating with a user;
memory storage means for storing executable instructions; and
computer processor means executing the instructions for implementing a plurality of safety controls including:
starting and stopping the stimulation therapy by starting the stimulation therapy after a predefined time delay but stopping the stimulation therapy instantaneously;
restricting stimulation therapy programming in response to a low-battery status of the electronic apparatus; wherein the low-battery status is triggered when a battery level of the electronic apparatus falls below a predetermined threshold that is above zero, and wherein the restricting comprises one or more of the following:
preventing the user from programming stimulation parameters;
preventing the user from activating a stimulation test; and
automatically stopping any existing stimulation test by shutting down the existing stimulation test gradually;
adjusting a value of a stimulation parameter of the stimulation therapy one predetermined step at a time, each adjustment corresponding to a separate user input; and
restricting a range in which the user can set an upper limit and a lower limit of the stimulation parameter.

10. The electronic apparatus of claim 9, wherein the user interface means comprises means for displaying a plurality of virtual objects and means for detecting a touch from the user, the touch corresponding to user engagement of one or more of the virtual objects.

11. The electronic apparatus of claim 10, wherein the starting and stopping the stimulation therapy comprises:
measuring an amount of time in which the user engages one of the virtual objects representing a starting of the stimulation therapy; and
starting the stimulation therapy after the amount of time exceeds the predefined time delay.

12. The electronic apparatus of claim 10, wherein the adjusting the value of a stimulation parameter is performed such that each separate user input includes a re-engagement of a respective one of the virtual objects by the user.

13. The electronic apparatus of claim 9, wherein the restricting the range in which a user can set the upper limit and the lower limit of the stimulation parameter comprises:
precluding the user from setting the upper limit to be less than a currently-set value of the stimulation parameter; and
precluding the user from setting the lower limit to be greater than the currently-set value of the stimulation parameter.

14. The electronic apparatus of claim 9, wherein:
the electronic apparatus is a clinician programmer;
the implantable medical device is a pulse generator; and
the user is a medical professional.

15. The electronic apparatus of claim 11, wherein the starting and the stopping of the stimulation therapy are performed in response to the same virtual object being engaged by the user.

16. The electronic apparatus of claim 9, wherein the starting of the stimulation therapy is always after the predefined time delay.

17. A method, comprising:
detecting a user input through a touch screen display of an electronic device configured to program a medical device implantable in a patient, wherein the detecting is performed at least in part by measuring an amount of time the touch screen display is engaged as a part of the user input;
determining whether the medical device is running a treatment for the patient when the user input is detected;
instructing the medical device to stop the treatment if the treatment is running, wherein the stopping of the treatment is performed immediately after the user input is detected;
instructing the medical device to start the treatment if no treatment is running and if the amount of time the touch screen display is engaged as a part of the user input exceeds a predetermined limit;
instructing the medical device to perform no treatment if the amount of time the touch screen display is engaged as a part of the user input does not exceed the predetermined limit;
determining whether the electronic device has a low-battery status; and
implementing one of the following measures in response to the low-battery status of the electronic device:
disabling programming of the electronic device;
stopping an ongoing treatment; and
preventing a prospective treatment.

18. The method of claim 17, wherein the treatment comprises one or more stimulation parameters, and further comprising:

changing a value of the one or more stimulation parameters by one predefined step at a time in response to one or more user actions.

19. The method of claim 18, wherein each change of the value of the one or more stimulation parameters corresponds to a different one of the user actions.

20. The method of claim 17, wherein the treatment comprises one or more stimulation parameters, and further comprising:
restricting a configurable range of an upper limit or a lower limit of one of the stimulation parameters.

21. The method of claim 20, wherein the restricting comprises:
restricting the configurable range of the upper limit of the stimulation parameter to be greater than or equal to a current value of the stimulation parameter; and
restricting the configurable range of the lower limit of the stimulation parameter to be less than or equal to the current value of the stimulation parameter.

22. The method of claim 17, wherein the detecting the user input comprises detecting a click of a virtual button on the touch screen display.

23. The method of claim 17, wherein the determining whether the electronic device has a low-battery status comprises:
continuously monitoring an amount of charge of a battery of the electronic device; and
deeming that the low-battery status has been achieved if the amount of charge of the battery is less than a predetermined amount of charge.

24. The method of claim 17, wherein:
the electronic device includes a portable handheld clinician programmer;
the user includes a healthcare personnel; and
the medical device includes a neurostimulator.

25. A method of implementing a plurality of safety controls via an electronic apparatus that is configured to program an implantable medical device to provide a stimulation therapy for a patient, the method comprising:
starting and stopping the stimulation therapy by starting the stimulation therapy after a predefined time delay but stopping the stimulation therapy instantaneously;
restricting stimulation therapy programming in response to a low-battery status of the electronic apparatus, wherein the low-battery status is triggered when a battery level of the electronic apparatus falls below a predetermined threshold that is above zero, and wherein the restricting comprises one or more of the following:
preventing the user from programming stimulation parameters;
preventing the user from activating a stimulation test; and
automatically stopping any existing stimulation test by shutting down the existing stimulation test gradually;
adjusting a value of a stimulation parameter of the stimulation therapy one predetermined step at a time, each adjustment corresponding to a separate input from a user; and
restricting a range in which the user can set an upper limit and a lower limit of the stimulation parameter.

26. The method of claim 25, further comprising:
displaying a plurality of virtual objects; and
detecting a touch from the user, the touch corresponding to a user engagement of one or more of the virtual objects.

27. The method of claim 26, wherein the starting and stopping the stimulation therapy comprises:
measuring an amount of time in which the user engages one of the virtual objects representing a starting of the stimulation therapy; and
starting the stimulation therapy after the amount of time exceeds the predefined time delay.

28. The method of claim 26, wherein the adjusting the value of a stimulation parameter is performed such that each separate user input includes a re-engagement of a respective one of the virtual objects by the user.

29. The method of claim 26, wherein the starting and the stopping of the stimulation therapy are performed in response to the same virtual object being engaged by the user.

30. The method of claim 25, wherein the restricting the range in which a user can set the upper limit and the lower limit of the stimulation parameter comprises:
precluding the user from setting the upper limit to be less than a currently-set value of the stimulation parameter; and
precluding the user from setting the lower limit to be greater than the currently-set value of the stimulation parameter.

31. The method of claim 25, wherein:
the electronic apparatus is a clinician programmer;
the implantable medical device is a pulse generator; and
the user is a medical professional.

32. The method of claim 25, wherein the starting of the stimulation therapy is always after the predefined time delay.

* * * * *